(12) United States Patent
Vilkomerson (10) Patent No.: US 6,346,081 B1
(45) Date of Patent: Feb. 12, 2002

(54) ANGLE-INDEPENDENT CONTINUOUS WAVE DOPPLER DEVICE

(75) Inventor: David Vilkomerson, Princeton, NJ (US)

(73) Assignee: Echocath Inc., Princeton, NJ (US)

( * ) Notice: Subject to any disclaimer, the term of this patent is extended or adjusted under 35 U.S.C. 154(b) by 0 days.

(21) Appl. No.: 09/522,799

(22) Filed: Mar. 10, 2000

Related U.S. Application Data (60) Provisional application No. 60/124,255, filed on Mar. 12, 1999.

(51) Int. Cl.[7] .................................................. A61B 8/00
(52) U.S. Cl. ....................................... 600/454; 600/457
(58) Field of Search ................................ 600/443, 447, 600/451, 455, 453, 454, 457

(56) References Cited

U.S. PATENT DOCUMENTS

| | | | | |
|---|---|---|---|---|
| 5,454,372 A | * | 10/1995 | Banjanin et al. | 600/454 |
| 5,544,658 A | * | 8/1996 | Kim et al. | 600/455 |
| 5,562,097 A | * | 10/1996 | Yao | 600/457 |

* cited by examiner

Primary Examiner—Marvin M. Lateef
Assistant Examiner—Maulin Patel
(74) Attorney, Agent, or Firm—Arthur L. Plevy; Duane Morris & Heckscher (57) ABSTRACT

An apparatus for determining the velocity of a fluid flowing through a lumen comprises a first diffraction grating transducer (DGT) responsive to a continuous wave (CW) input and operable in a first mode for producing a first signal beam at a first frequency and first phase, and in a second mode for producing a second signal beam at the first frequency and a second phase; a second diffraction grating transducer (DGT) operating as a receiver and coupled to the first diffraction grating transducer at a predetermined angle, the second diffraction grating transducer producing a first beam which intersects the first DGT first beam for receiving a first reflected signal associated with the first signal beam, and for producing a second beam which intersects the first DGT second beam for receiving a second reflected signal associated with the second signal beam; the first beams adapted to intersect in a first predetermined region through which dynamic particles are undergoing velocity analysis, and the second beams adapted to intersect in a second predetermined region through which dynamic particles are undergoing velocity analysis; and electronic circuitry responsive to the first and second reflected signals for comparing with the first frequency and the first and second phase to determine the velocity of the fluid.

20 Claims, 9 Drawing Sheets

RELATIVE SENSITIVITY vs DEPTH, 4.76 mm TUBE, IN TISSUE-MIMICKING MATERIAL

FIG. 10

ANGLE-INDEPENDENT CONTINUOUS WAVE DOPPLER DEVICE

CROSS-REFERENCE TO RELATED APPLICATIONS

This application claims priority from commonly assigned, copending U.S. Provisional Patent Application No. 60/124,255 filed Mar. 12, 1999, entitled "ANGLE-INDEPENDENT CONTINUOUS WAVE DOPPLER DEVICE" which is incorporated herein by reference in its entirety and for all purposes.

FIELD OF THE INVENTION

The present invention relates to diagnostic medical devices which utilize ultrasound to determine the direction and speed of a fluid flowing in a vessel, and more particularly to continuous wave Doppler systems for measuring blood flow.

BACKGROUND OF THE INVENTION

Figure 1:
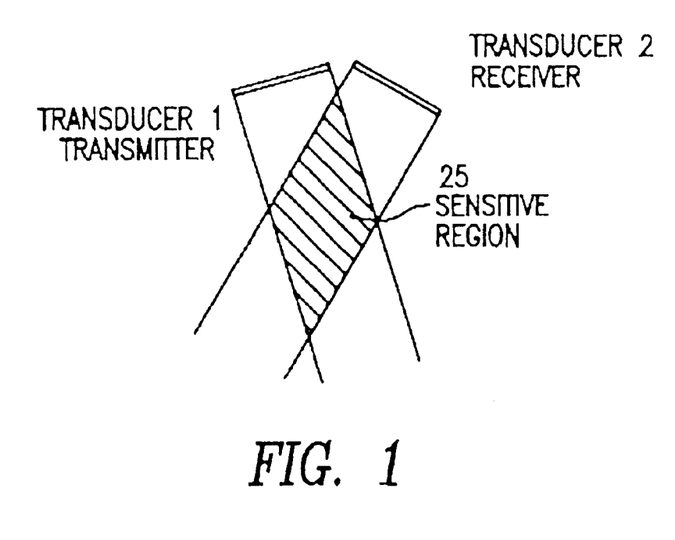
FIG. 1 is a schematic illustration of a two transducer continuous wave (CW) Doppler system showing a sensitive region defined as an area where the transmitting and receiving beams coincide.

The simplest and most widely used Doppler systems to measure blood flow are "CW" (Continuous Wave) Doppler Probes. As shown in FIG. 1, a CW Doppler probe consists of two transducers 1 and 2, one continuously excited by a driving source (transducer 1), and the other continuously receiving (transducer 2).

The signals received by the second transducer can only originate where the first transducer's "beam" (the region in space where the first transducer produces acoustic energy) intersects the second transducers "beam" (the region of space from which the transducer is sensitive, analogous to an antenna's beam plot). These "send beams" and "receive beams" are identical for identical transducers by the principle of reciprocity, as is well-know in the state of the art.

In a CW Doppler system, the signal from transducer 2, the receiving transducer in FIG. 1, is filtered so that only signal energy at frequencies that have been Doppler-shifted away from the frequency transmitted by transducer 1 are further processed. One such method is known, where the received signal is heterodyned by the same frequency transmitted and a high-pass filter allows only difference frequencies to be passed. There are a number of such methods that are well-known, and may be found, for example, in "Doppler Ultrasound and Its Use in Clinical Measurement", by P. Atkinson and J. P. Woodcock, Academic Press, London, 1982. (Electronic circuits for physical embodiments of CW Doppler systems are also shown there.) As is well known, the magnitude of the Doppler shift is related to the velocity of the moving material, e.g. blood, which causes Doppler shifted signals. Also, the power present at a particular frequency is proportional to the amount of transmitted power intercepted by the moving backscattering material and the efficiency of backscattering. For blood, for example, the amount of energy at different frequencies is related to the amount of blood moving at the corresponding velocity in the region where the transmitting and receiving beams coincide. (This region where the beams coincide is often described as the "sensitive region" in CW Doppler systems.)

That only blood moving in the sensitive region produces a signal in CW Doppler systems is both a strength and a liability. It is a strength in that there is no requirement for selecting a "sample gate" as in pulsed wave Doppler systems, but a liability in that the sensitive volume is determined by the beam pattern of the transducers used and their geometrical arrangement, rather than by the setting of a sample gate. The simplicity in use of CW Doppler, as well as the simplicity of the system as a whole, has made CW Doppler a very widely used method of determining motion, in particular that of blood for medical purposes.

A significant drawback of Doppler blood measurement, however, is that the Doppler-shift frequency is proportional to the velocity of the blood multiplied by the cosine of the angle between the velocity vector and the beam. Therefore, Doppler measurements of blood velocity do not give absolute velocity values, but rather only relative values.

It is known that by using two or more beams at known angles to each other to insonate moving blood, two Doppler shift equations may be generated which contain the two unknowns of the velocity of the blood and the angle of the transducer to the velocity. Accordingly, since there are two (or more) equations with two unknowns, using algebra produced the velocity and the angle, independent of the angle of the transducer to the velocity vector.

A number of patents employ variations of this technique using multiple transducers at fixed angles to each other and using pulsed Doppler. Such patents include, U.S. Pat. No. 5,738,097, issued to Beach et al. U.S. Pat. No. 4,062,237 issued to Fox, used CW Doppler instead of pulsed Doppler, by employing multiple sets of transducers that operate at different frequencies from each other. Since each of the above patents disclose methods which demand multiple transducers that require significant electronic and mechanical alignment, these methods have not been found clinically useful.

It is also known that, by using a special transducer, namely a diffracting-grating transducer, multiple beams at known angles to each other may be produced. Commonly assigned U.S. Pat. Nos. 5,488,953 and 5,540,230 issued to the present inventor Vilkomerson, and incorporated herein by reference, disclose such a transducer and teach a method of determining the velocity and angle from these beams originating from the same transducer. Using a diffraction grating transducer structure and the disclosed method allows the velocity to be determined independently of the angle of the transducer to the blood velocity.

However, the system described in the previously mentioned patents still required pulsed Doppler operation, with the attendant need to set a sample gate to the region of interest. In the present invention there is disclosed a method of using diffracting-grating transducers in a CW Doppler system that does not require setting a sample gate, just like conventional CW Doppler systems, but provides angle-independent velocity determination with two transducers. Also disclosed are a number of other useful structures for angle-independent CW Doppler use.

As the previously mentioned patents teach how the information from the multiple beams is used to calculate the velocity of the moving blood (and if required the angle of the transducer to the blood vessel), what will be considered herein is the arrangement of transducers so as to obtain the multiple beam insonation needed to utilize those methods to calculate the blood velocity, but without the need to set a sample gate, i.e. using CW rather than pulsed Doppler.

SUMMARY OF THE INVENTION

A method of using diffracting grating transducers in a CW Doppler system for providing angle independent velocity determination. Such method is accomplished using only two transducers. An apparatus for determining angle-independent velocity comprising diffracting grating transducers operating in CW mode is also disclosed.

A method and apparatus for providing angle-independent CW probe operation obtained without diffraction-grating transducers is also disclosed.

An apparatus for determining the velocity of a fluid flowing through a lumen comprises a first diffraction grating transducer (DGT) responsive to a continuous wave (CW) input and operable in a first mode for producing a first signal beam at a first frequency, and in a second mode for producing a second signal beam at the first frequency; a second diffraction grating transducer (DGT) operating as a receiver and related to the first diffraction grating transducer at a predetermined angle (the "dihedral angle"), the second diffraction grating transducer producing a first receiving beam which intersects the first DGT first beam for receiving a first reflected signal associated with the first signal beam, and for producing a second receiving beam which intersects the first DGT second beam for receiving a second reflected signal associated with the second signal beam; the first beams adapted to intersect in a first predetermined region through which dynamic particles are undergoing velocity analysis, and the second beams adapted to intersect in a second predetermined region through which dynamic particles are undergoing velocity analysis; and electronic circuitry responsive to the first and second reflected signals for comparing with the first frequency to determine the velocity of the fluid.

A method for determining the velocity of a fluid flowing through a luen comprising directing a CW transmitting first diffraction grating transducer toward the lumen; directing a CW receiving second diffraction grating transducer toward the lumen, the first and second CW diffraction grating transducers oriented at a predetermined angle from one another such that corresponding edges of the DGTs converge to define an apex, producing first and second signal beams, respectively from each of the first and second DGTs which intersect at portions of the lumen, the first signal beam resulting from the first DGT transmitting at a first frequency and first phase, and the second signal beam resulting from the first DGT transmitting at the first frequency and second phase; the first and second signal beams resulting from the second DGT being Doppler shifted signals associated with the first DGT first signal beam and the first DGT second signal beam respectively, and determining the fluid velocity flowing through the lumen based on the Doppler shifted signals, the first frequency and the diffracting angle of the DGT.

There is also embodied in the present invention an apparatus for determining the velocity of blood flowing through a lumen comprising a first pair of continuous wave non-diffraction grating transducers coupled at a first dihedral angle relative to one another, the first pair of transducers producing beams which intersect at a given point which defines a sensitive volume; a second pair of continuous wave nondiffraction grating transducers coupled at the first dihedral angle relative to one another; the second pair of transducers producing beams which intersect at the given point, the first and second pairs of transducers oriented at a second angle B relative to one another; a signal source for driving the first and second pairs of transducers to cause one of the first pair to be driven at a first frequency and one of the second pair to be driven at the first frequency; whereby the other of the first pair receives a first reflected signal shifted in frequency relative to the signal from the first pair transmitting transducer, and whereby the other of the second pair receives a second reflected signal shifted in frequency relative to the signal from the second pair transmitting transducer; and electronic circuitry coupled to the first and second pairs of transducers for determining the velocity of the blood taking into account the frequency shifted reflected signals and driving signal frequencies, dihedral angles of the pairs of transducers, and angle B between the first and second pairs of transducers.

Also embodied in the present invention is a method of determining the velocity of a lumen comprising orthogonally orienting a first pair and a second pair of diffraction grating transducers relative to one another, each transducer of the first and second pairs positioned substantially adjacent one another and having edges converging toward one another so as to form dihedral angles, each the pair of transducers oriented so as to have intersecting beams which produce a sensitive volume around the lumen; driving a corresponding one of the first and second pairs of transducers to transmit at a first frequency such that a reflected signal indicative of the first frequency is received by the other of the first and second pairs; adjusting the driving frequency by a predetermined amount and driving the corresponding one of the first and second pairs of transducers to transmit the adjusted frequency such that a reflected signal indicative of the adjusted frequency is received by the other of the first and second pairs; determining the velocity in the two orthogonal directions based on the frequencies and dihedral angles for each of the first and second pairs of transducers; and calculating the velocity of the blood based on the velocity in the two orthogonal directions.

BRIEF DESCRIPTION OF THE DRAWINGS

The invention is to be explained in more detail below based on embodiments depicted in the following figures where.

DETAILED DESCRIPTION OF THE INVENTION

Figure 2A:
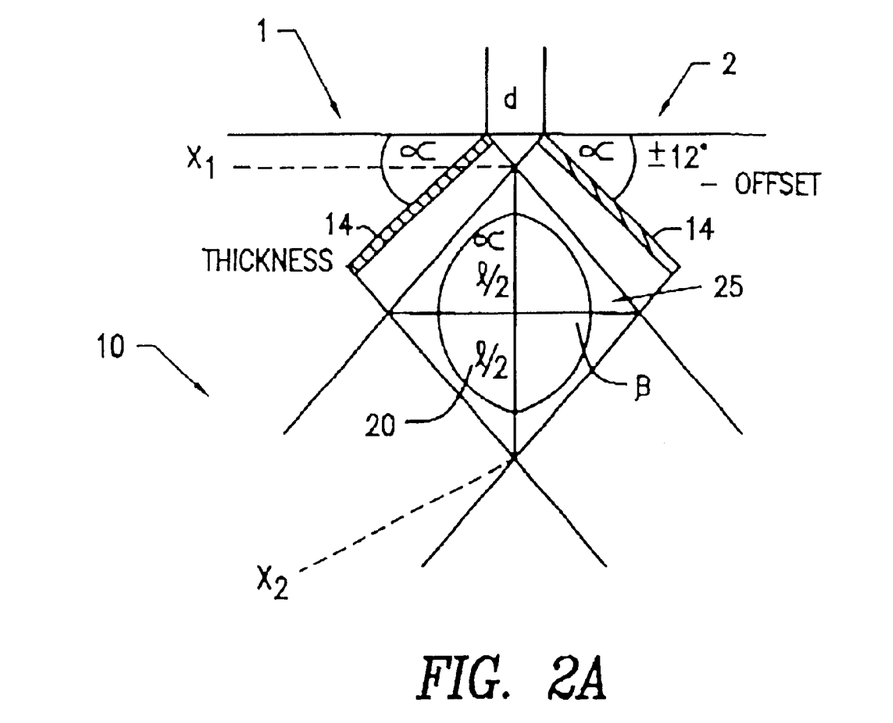
FIGS. 2A and 2B illustrate side and top views respectively of a continuous wave angle independent Doppler device according to the present invention.
Figure 2B:
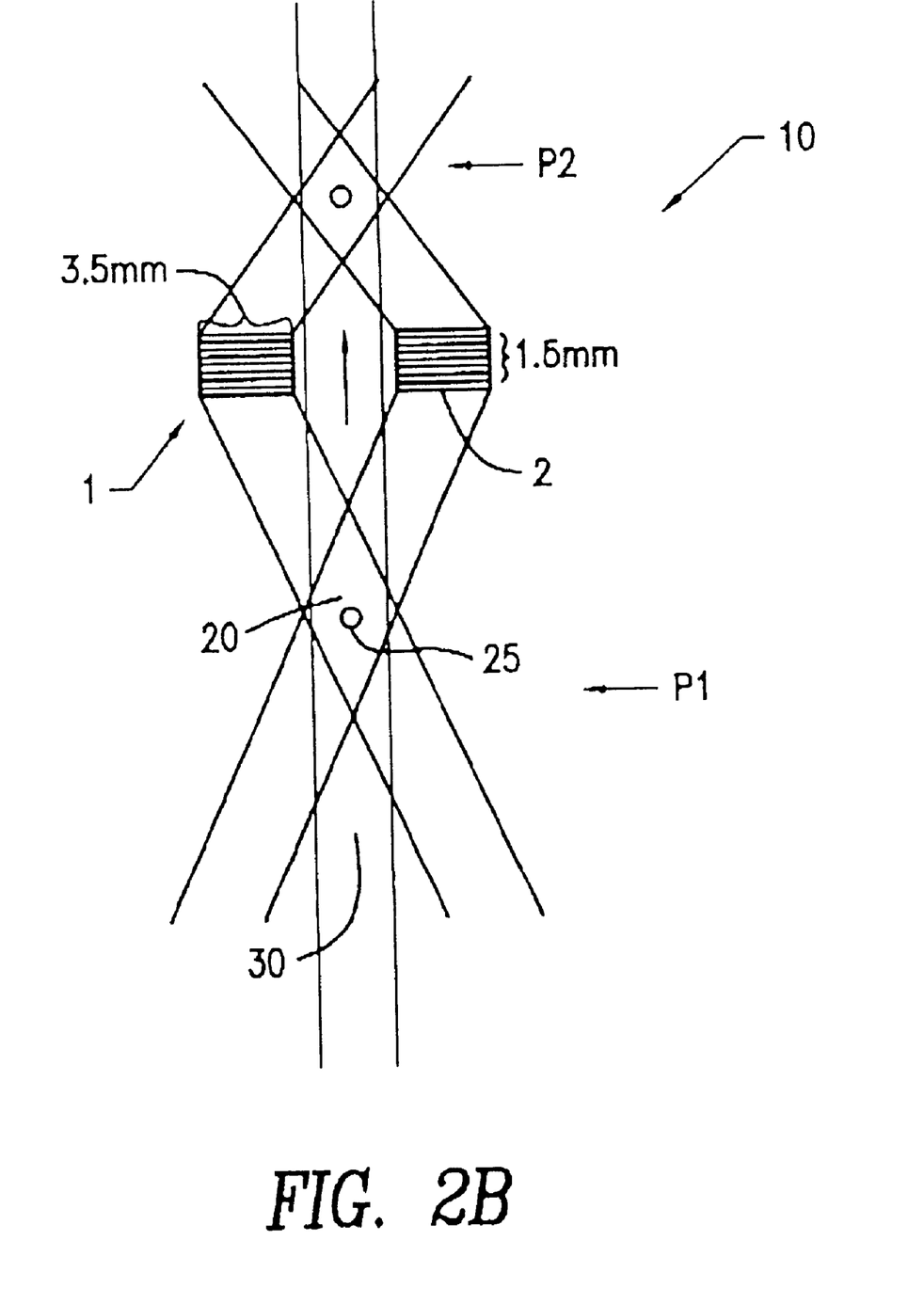
Figure 3A:
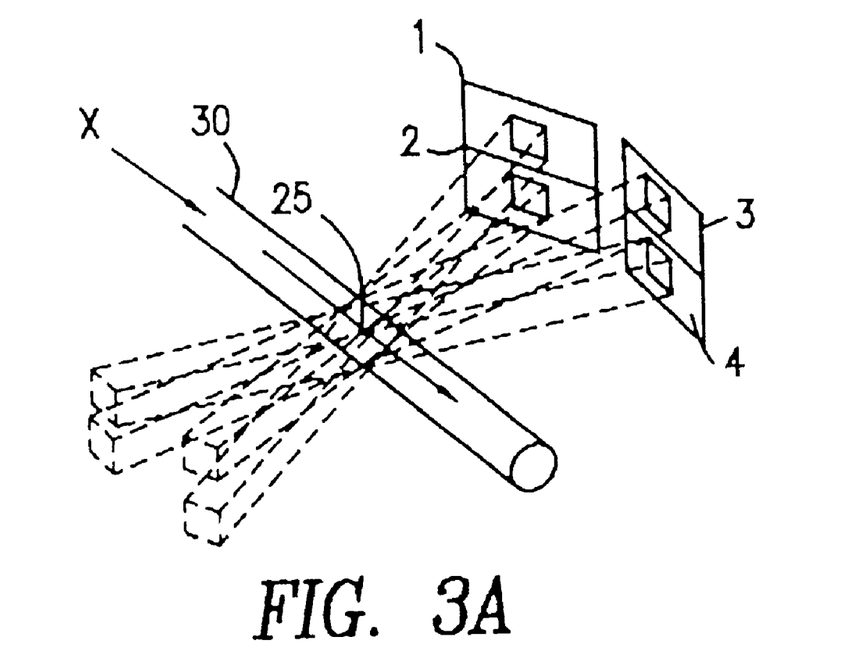
FIG. 3A illustrates a perspective view of a set of non-diffracting grating transducers operating in a CW mode according to an alternate embodiment of the present invention.
Figure 3B:
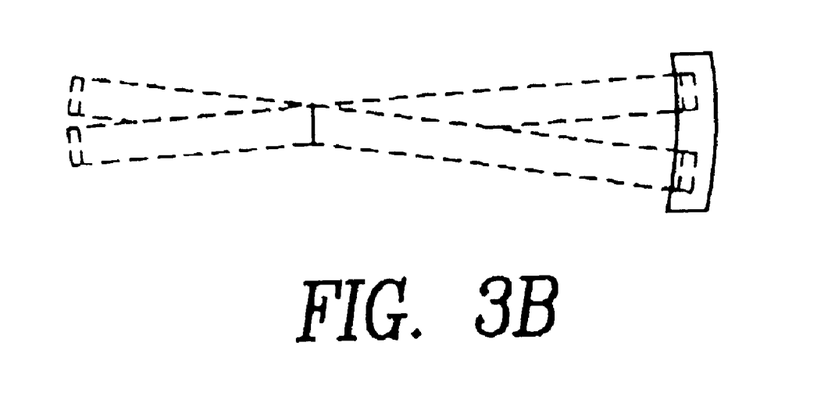
FIG. 3B shows a side view of the non-diffracting grating transducers of FIG. 3A.
Figure 3C:
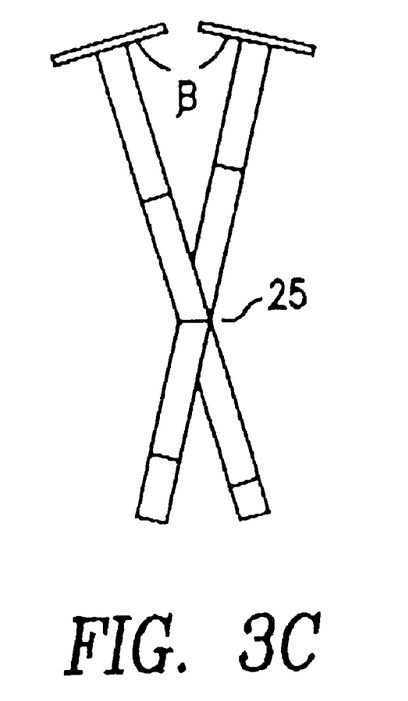
FIG. 3C shows a top view of non-diffracting grating transducers illustrated in FIG. 3A.
Figure 3D:
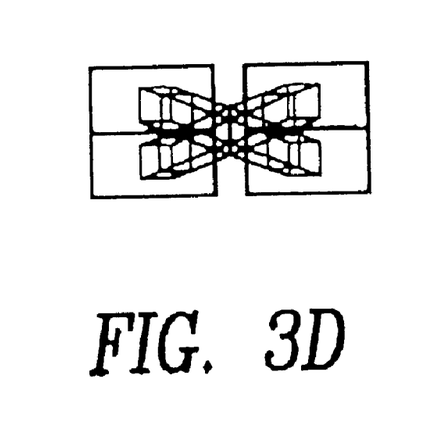
FIG. 3D shows a back end view of the system employing the two sets of non-diffracting grating transducers shown in FIG. 3A.

Referring now to FIGS. 2A and 2B, there is shown a CW angle-independent Probe 10 according to the present invention. It consists of two diffraction-grating transducers, 1 and 2, one sending the one receiving, as in a conventional CW Doppler structure. However, the effect of the small "dihedral" angle α, visible in the side view, is to make the beam cross the plane of 20 the blood vessel 30, as seen in the top view. The mirror-image receiving transducer 2 has its receiving beam pattern similarly crossing the plane of the blood vessel. The sensitive volume 25, therefore, is where the beams cross. By the use of geometry, or by drawing the beam volume, the location and dimensions of the sensitive volume can be determined.

For example, for a 10 MHz system suitable for superficial vessels, the grating transducers would be 1.5 mm wide (corresponding to 5 cycles of grating, as described in U.S. Pat. No. 5,488,953 which produces a beam at 30° to the perpendicular to the face of the transducer) and 3.5 mm long. With a 12° dihedral, and a 1 mm separation distance d between the two diffracting-grating transducers, the sensitive volume 25 would extend from point x1 of 2.4 mm (measuring from the top point of the transducer) to point x2 of 19.2 mm, in a trapezoidal shape as shown, with the maximum width of 3.6 mm. Preferably, the distance d is small but not zero to allow independent mechanical vibration of the transducers. However, in certain applications, it may be desirable to have the gap or separation distance relatively large depending on where one wishes to position the sensitive volume. This is because the sensitive volume has a depth in the longitudinal plane, e.g. x1, given by d/2*tan α. If the dimensions are changed, for example, if the dihedral angle is made smaller, the sensitive volume dimension will change, with the top of the sensitive volume, given by d/2*tan α, moving down and the bottom of the sensitive area, which is transducer length/sin α deeper than the top, even more so; for example, if the dihedral angle is made 6°, the top point x1 will move down about 2.4 mm, i.e. to 4.8 mm from the top, and the bottom, x2, about 19 mm, i.e. to 38.2 from the top. Use of these formulae and geometry or modeling can easily be used to calculate the effect of the various transducer dimensions and parameters on the sensitive volume dimensions and location and contemplated to be well within the level of the skilled artisan.

Figure 5:
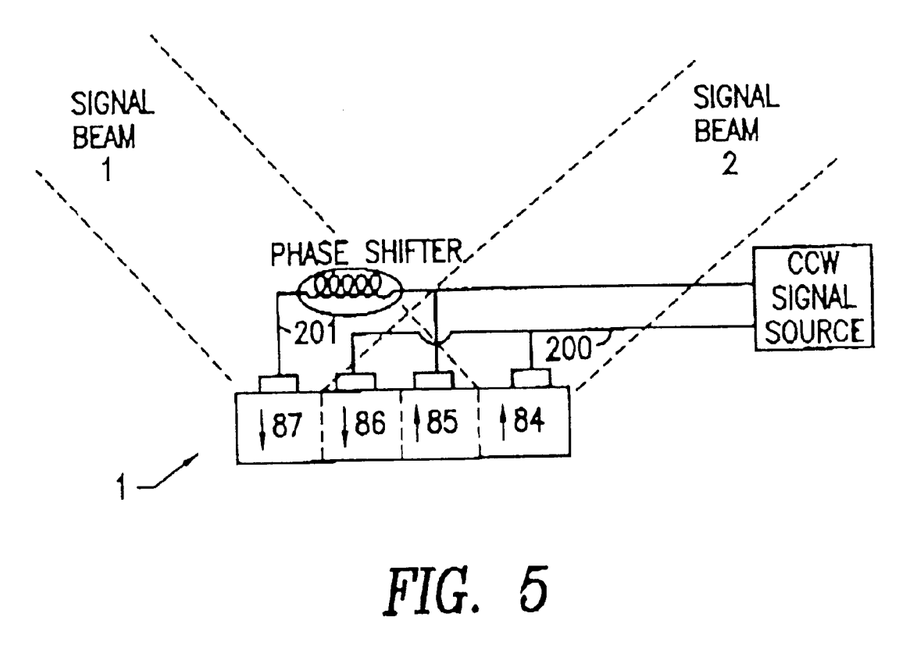
FIG. 5 illustrates a high level block diagram illustrating the phase shifting operation of the diffraction grating transducers to produce two beams according to the present invention.
Figure 6:
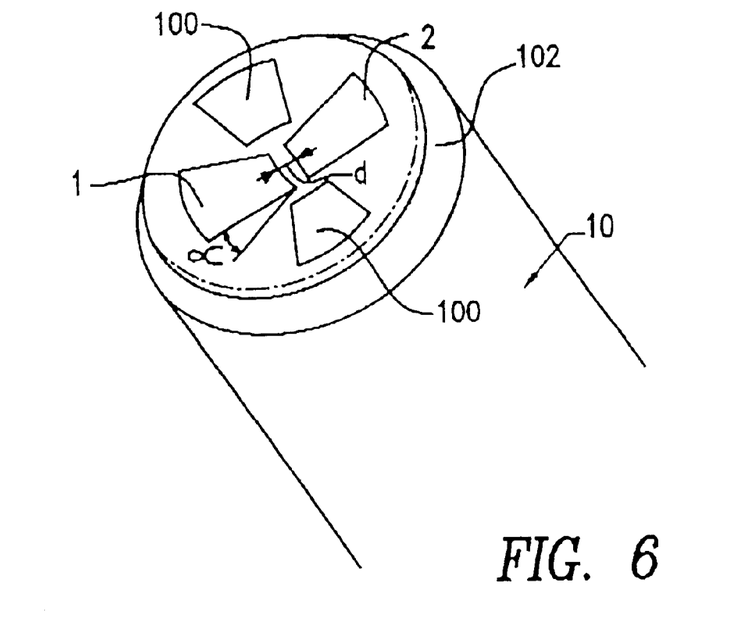
FIG. 6 provides an exemplary illustration of a probe device incorporating two diffraction grating transducers according to an aspect of the present invention.
Figure 7:
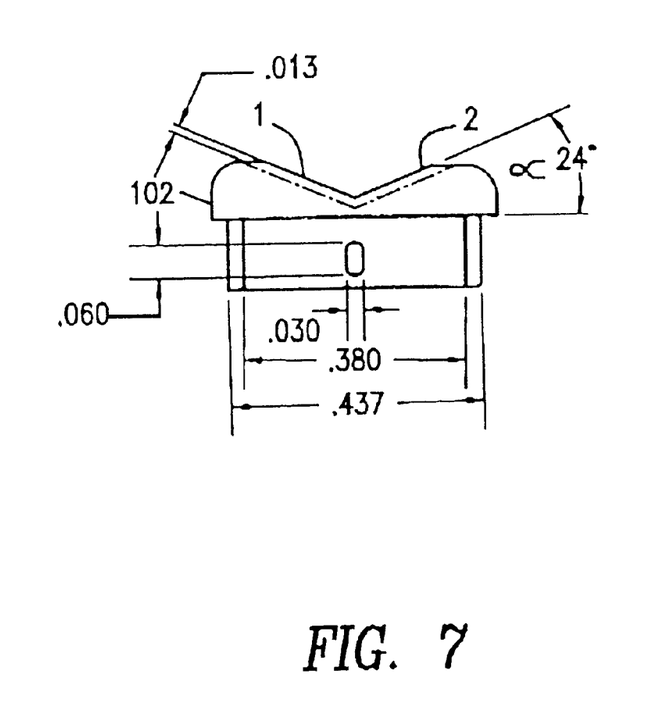
FIG. 7 provides a side view of the cap portion of the probe shown in FIG. 6.
Figure 8A:
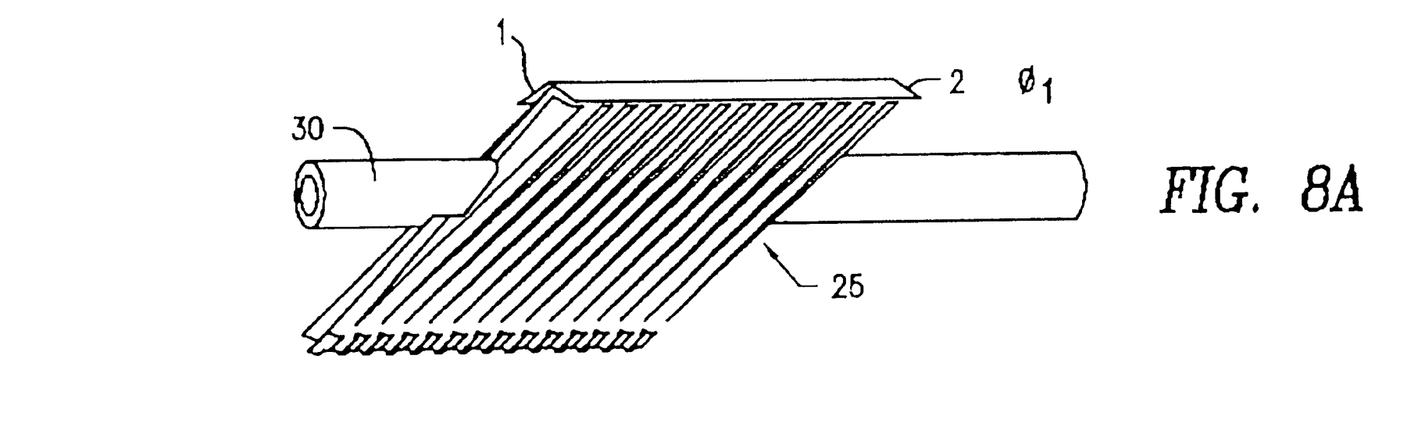
FIGS. 8A and 8B provide perspective views of the operation of DGTs in "flip" mode for sensing the velocity of blood by beams at a first angle and at a second angle, respectively.
Figure 8B:
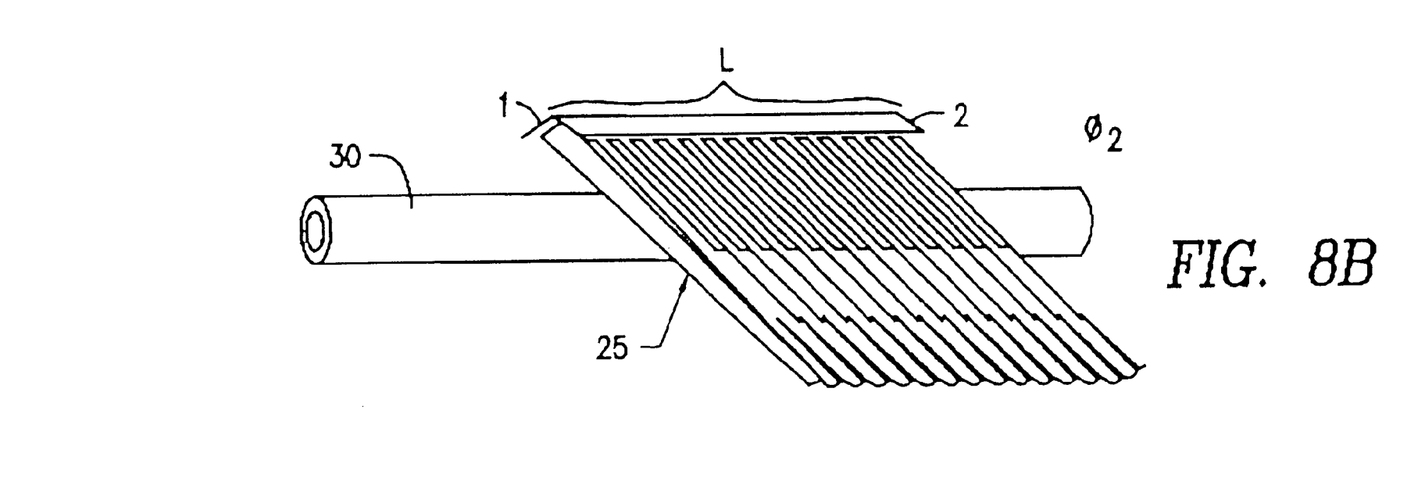

The special characteristic of the diffracting-grating transducer is that the beam angle can be changed. Therefore, as taught in the earlier patents incorporated herein by reference, if the relative phase of the two subgrids of the diffracting-grating transducer are altered by 90°, the beams will "flip", i.e. as shown in the top view, the beam transmitting beam will point backward (point P2) if previously it had pointed forward (point P1). FIGS. 8A and 8B provide perspective views of the operation of DGTs 1 and 2 for sensing the velocity of blood at a first angle (FIG. 8A) and at a second angle (FIG. 8B). An exemplary transducer structure which implements the above described phase shifting technique is depicted in FIG. 7 of U.S. Pat. No. 5,540,230, the subject matter of which is incorporated herein by reference in its entirety. FIG. 5 illustrates a high level block diagram illustrating the phase shifting of each of the subgrids 200 and 201 comprising elements 84, 85 and 86, 87 respectively. Note that the above provides an exemplary illustration of generating two signals of a given frequency shifted in phase by a predetermined phase amount. Other well-known structures for phase shifting the signal beam are contemplated. On the receiving side, similar well known phase shifting of the transducer elements are utilized to receive the Doppler shifted reflected signals transmitted by transducer 1, and thus will not be described in further detail. As the phase-shifters of the receiving diffraction-grating transducer are similarly changed, the sensitive volume 25 moves, and a second CW frequency-shift can now be measured. As is well known, the velocity of the blood in the vessel can now be determined, independently of the angle of the plane of the transducer to the angle of the blood vessel. (It is assumed that the blood velocity does not change between the two measurements, which as it can take place within a few tens of microseconds of each other, is a reasonable assumption; this assumption is used in the following examples as well). As is clear from the drawing, the axis of the blood vessel must be aligned, or nearly so, with the axis of the CW diffraction-grating transducers, and the measured Doppler-shift is that along the axis of the transducers. FIG. 6 provides an exemplary illustration of the probe device or apparatus 10 comprising diffraction grating transducers 1 and 2 separated via distance d from one another and positioned at a given dihedral angle α. Preferably, the dihedral angle is 12 or 24 degrees, however, it is contemplated that the range of dihedrals may be between 1 and 89 degrees depending on the desired application and the volume to be generated. Electronic circuitry 100 is coupled to each of the line diffraction grating transducers 1 and 2 for signal processing in well known manner. Note that the receiving circuitry includes signal processing circuitry for receiving, conditioning and analyzing, the received signals and represents conventional signal processing and comparison circuit modules well known in the art. FIG. 7 provides a side view of the cap portion 102 shown in FIG. 6 illustrating the orientation of the DGTs 1 and 2 within the cap and having a dihedral angle α of 24 degrees. Note that while the preferred embodiment shows a transducer arrangement where the dihedral angles are fixed, an alternative embodiment would include a variable dihedral angle whereby the transducers would be actuated by pivoting a screw mechanism within the probe cap, for example, in order to change the dihedral angles and thus change the sensitive volume.

Figure 8C:
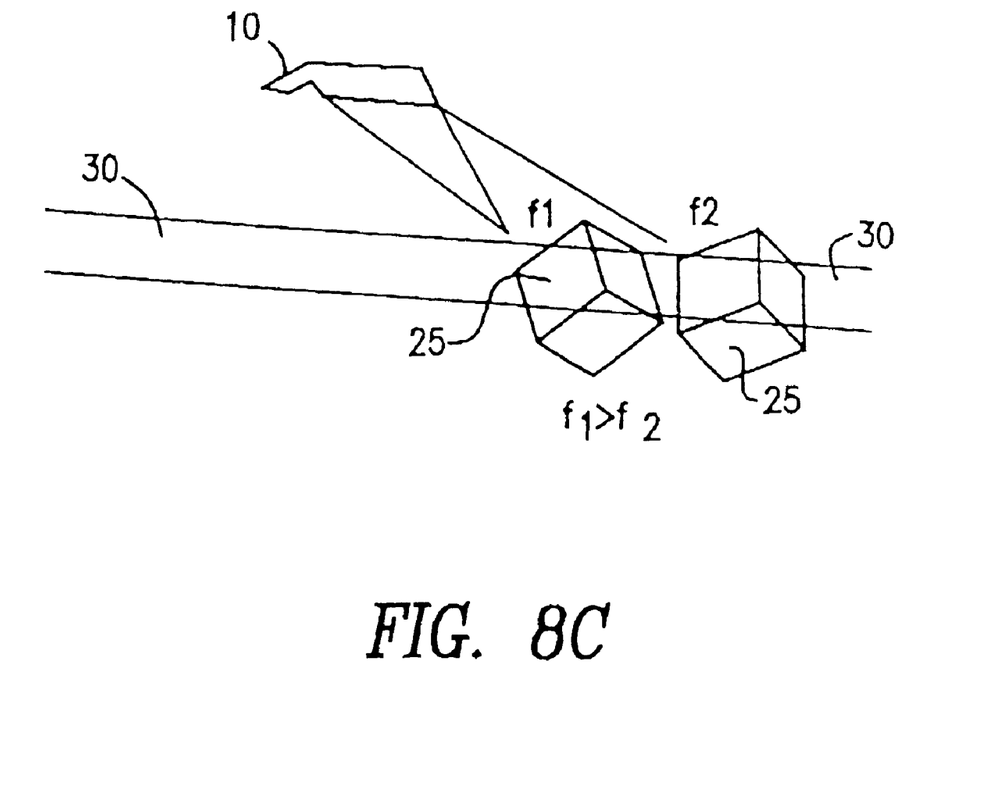
FIGS. 8C illustrates the movement of the sensitive volume along the vessel according to a change in frequency of the DGTs.
Figure 9:
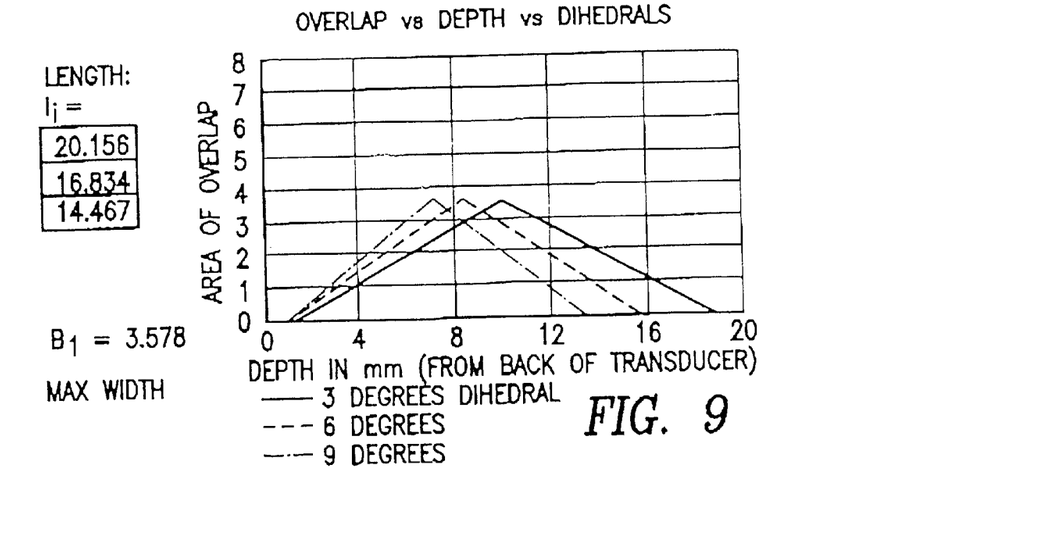
FIG. 9 is an exemplary diagram illustrating overlap of the sensitive region versus depth and as a function of dihedral angle.
Figure 10:
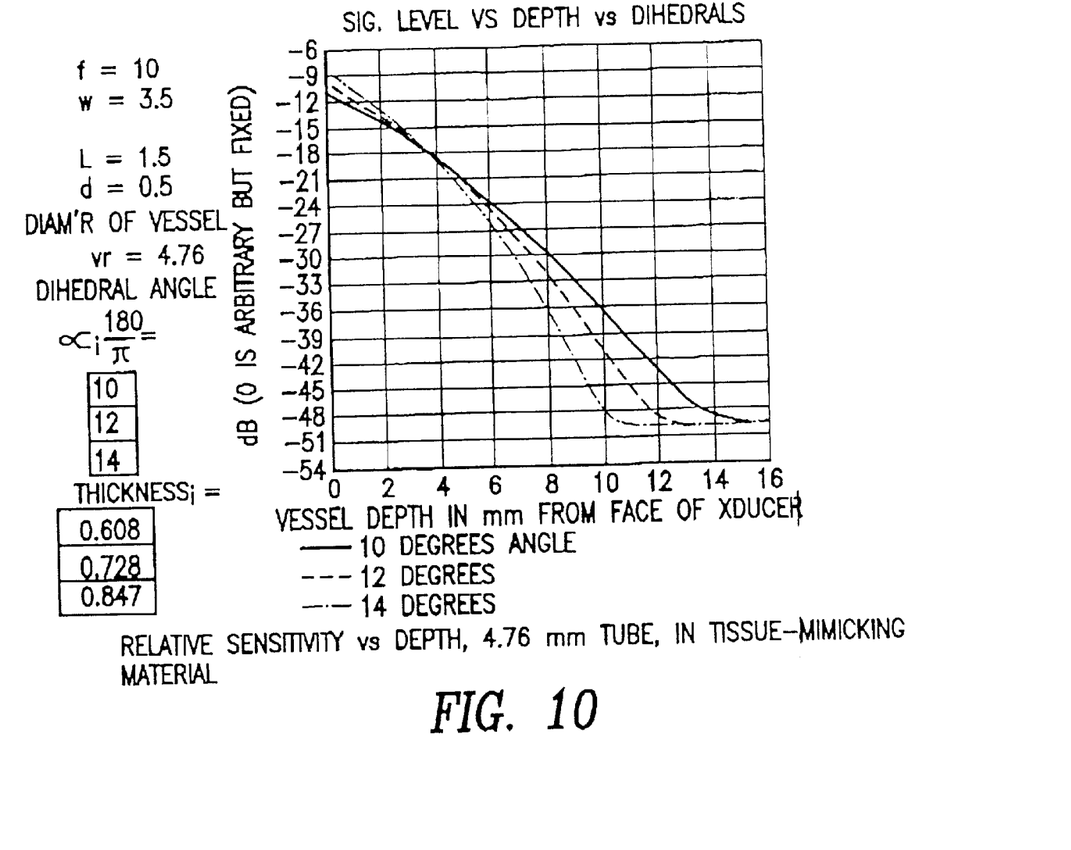
FIG. 10 is an exemplary diagram of the signal level versus depth and as a function of dihedral angle.

As discussed in the above-mentioned patents, another way of altering the beam direction is to change the frequency referred therein as the "wiggle" mode. As the beam angle would change, the position of the sensitive volume would also change, but in distinction from changing the phase direction, the sensitive volume would stay on the same side of the transducer, moving either closer or further from the transducers in the top view of FIG. 2B. FIG. 8C illustrates how the sensitive volume would move along the vessel according to a change in frequency f1, f2. Note that, the higher the frequency, the less beam diffraction. Using the wiggle mode allows easier alignment with the vessel, but requires a broad-band diffraction grating transducer which is not necessary for the flip-mode obtained by changing the phase.

It should be noted that as the diffraction-grating transducer is a linear system and the principle of superposition holds, two frequencies can be used simultaneously, if they are separated sufficiently in frequency that the back-scattered Doppler signals can be separated by electronic filters. Thus, the two measurements for the two sensitive volumes can be accomplished simultaneously. As the Doppler shifts for blood at 10 MHZ are in the order of 10–20 KHz, and the bandwidth of the diffraction-grating transducers are in the order of MHZ's, this may be easily accomplished. An example of a transducer system employing a group of electronic filters for filtering and synthesizing back scattered energy is described in commonly assigned patent application Ser. No. 09/256,633 entitled "MULTI-BEAM DIFFRACTION GRATING IMAGER APPARATUS AND METHOD" incorporated herein by reference.

It should also be noted that the depth of the sensitive volume below the plane of the transducer changes with the diffracting angle of the transducer. The overlap point, where the beams first cross, is a constant distance from the transducers However, if the beam is diffracted at a higher angle from the transducer, the overlap point will occur closer to the surface. This must be considered in using these diffracting-grating transducer probes in multi-frequency operation, to make sure that the sensitive volume does not move away from the vessel when the frequency changes.

If broad-band transducers are used in the flip mode, the change in height of the sensitive volume can be used to adjust the position of the sensitive volume, (i.e. higher or lower) compared to the plane of the probe, by changing the frequency. This electronic control of the location of the sensitive area can be useful in ensuring that a vessel of a particular depth is measured.

It should also be noted that this angle-independent CW probe operation can also be obtained without diffraction-grating transducers. As shown in FIG. 3A–3D, by using four conventional CW transducers, each pair with a small dihedral angle α and a larger angle B in the orthogonal direction, two sets of CW measurement with different insonation angles can be obtained. For example, in FIG. 3A–D, if transducer 1 is driven at frequency f1 and transducer 2 receives the blood-scattered signal from the overlap region 25 shown, and the Doppler-shift is measured, and then transducer 3 used for transmitting f1 and transducer 4 as receiving, another Doppler-shift frequency is obtained. As previously taught, the velocity can now be calculated independently of the plane of the four transducers in relation to the axis X of the blood vessel. The need for four transducers in this configuration makes such a CW probe more complicated, unwieldy, and expensive than the above-described use of diffraction-grating transducers. It would also be possible, if somewhat more clumsy, if rather than having the X structure of beams visible in FIG. 3, all four beams could point "upstream", but at different angles; this mode would operate in a manner analogous to the "wiggle" mode described above.

While all the structures for CW Doppler angle-independent measurements described are for independence of the angle of the plane of the transducer to the plane of the vessel to be measured, the transducers must be oriented so that the sensitive volume moves along the axis of the vessel, i.e. that the change in angle of the beam must be along the axis of motion. This can be accomplished by noting when the power in the two beams is equal, or if the vessel is visible, just by aligning the structure to the vessel.

Figure 4:
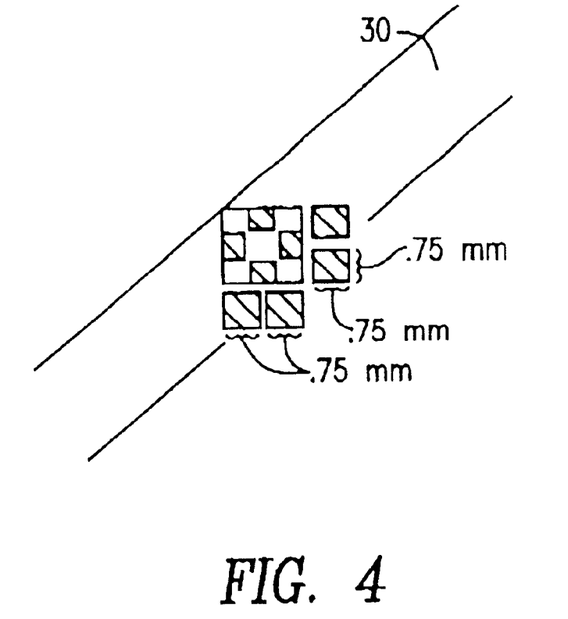
FIG. 4 shows a top down view of two sets of diffracting grating transducers oriented perpendicular to one another for calculating blood velocity independent of the plane of the transducers or their orientation according to another embodiment of the present invention.

In some circumstances, however, it may be desirable that the CW probe can measure the velocity without orienting the probe so that the movement of the sensitive volume is along the vessel. FIG. 4 provides a schematic illustration of how this may be accomplished: two sets (1,2) and (3,4) of diffracting-grating transducers, each operating in the wiggle mode, are set up orthogonally to one another. Each pair or set represents an orthogonal set which detects blood motion that would be perpendicular to their grating structure, or equivalently, parallel to the space between the two transducers set at the dihedral angle. The velocity in the two orthogonal directions would be determined by using each pair in turn for its two measurements, and the orthogonal vector calculated. Summing the squares of the two velocity components and calculating the square root would give the vector velocity, independent of the plane of the transducer or its orientation.

This structure would work best with high frequency transducers, (e.g. transducers operating at least at 20 MHZ. With such transducers, the linear dimensions of the transducers would be 1 mm or less, so the size of the sensitive volume would be small enough to move and still be within the lumen of the vessel to be measured. For example, at 20 MHZ, if the wiggle mode used a 45° and 35° beam at 3 mm depth, the motion of the sensitive volume along its axis would be only 0.9 mm. Therefore, if the vessel were several millimeters in size, the square shown outlined in FIG. 4, representing the motion of the sensitive volume, would be slightly larger than a square millimeter.

In this manner, by the use of diffracting-grating transducers, and in some configurations conventional transducers, that allow angle-independent CW measurements to be obtained.

While there has been shown and described the preferred embodiments of the invention, other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

What is claimed is:

1. An apparatus for determining the velocity of a fluid flowing through a lumen comprising:
   a first diffraction grating transducer and a second diffraction grating transducer operable in a first mode for providing a first cooperating pair of intersecting ultrasonic beams; the first diffraction grating transducers responsive to a continuous wave signal for driving the first diffraction grating transducer at a first frequency and first phase, the first and second diffraction grating transducers operable in a second mode for providing a second pair of cooperating intersecting ultrasonic beams, the first diffraction grating transducer responsive to a continuous wave signal for driving the first diffraction grating transducer at a first frequency and second phase, the second diffraction grating transducer operative as a receiver for receiving reflected signals associated with the first and second signal beams
   means for focusing the intersecting beams to intersect in a first predetermined region of the lumen through which dynamic particles are undergoing velocity analysis, and the second beams to intersect in a second predetermined region of the lumen through which dynamic particles are undergoing velocity analysis; and
   means responsive to the reflected signals for comparing with the first frequency and the first and second phase to determine the velocity of the fluid.

2. The apparatus according to claim 1 further comprising means coupled to the first and second transducers for switching between the first and second modes.

3. The apparatus according to claim 1, wherein the first and second modes operate simultaneously.

4. The apparatus according to claim 1, wherein the first and second diffraction grating transducers are positioned substantially adjacent to one another and having edge portions converging towards one another defining an apex.

5. The apparatus according to claim 4, wherein the edge portions converging toward one another defining the apex are separated by a predetermined distance.

6. An apparatus for determining the velocity of a fluid flowing through a lumen comprising:

a first diffraction grating transducer (DGT) responsive to a continuous wave (CW) input and operable in a first mode for producing a first signal beam at a first frequency and first phase, and in a second mode for producing a second signal beam at the first frequency and a second phase;

a second diffraction grating transducer (DGT) operating as a receiver and coupled to the first diffraction grating transducer at a predetermined angle, the second diffraction grating transducer producing a first beam which intersects the first DGT first beam for receiving a first reflected signal associated with the first signal beam, and for producing a second beam which intersects the first DGT second beam for receiving a second reflected signal associated with the second signal beam;

means for focusing the first beams to intersect in a first predetermined region through which dynamic particles are undergoing velocity analysis, and the second beams to intersect in a second predetermined region through which dynamic particles are undergoing velocity analysis; and means responsive to the first and second reflected signals for comparing with the first frequency and the first and second phase to determine the velocity of the fluid.

7. The apparatus according to claim 6, wherein the predetermined angle is a dihedral angle.

8. The apparatus according to claim 7, wherein edges of the first and second DGTs converge to from a tent-like shape.

9. The apparatus according to claim 8, wherein the converging edges of the first and second DGTs are separated from one another by a predetermined distance.

10. The apparatus according to claim 6, wherein the value of the dihedral angle is indicative of the location of the first and second predetermined regions.

11. The apparatus according to claim 5, wherein the first and second phases differ by substantially 90 degrees.

12. A method for determining the velocity of a fluid flowing through a lumen comprising:

directing a CW transmitting first diffraction grating transducer toward the lumen;

directing a CW second diffraction grating transducer toward the lumen, the first and second CW diffraction grating transducers oriented at a predetermined angle from one another such that corresponding edges of the DGTs converge to define an apex, producing first and second signal beams, respectively from each of the first and second DGTs which intersect at portions of the lumen, the first signal beam resulting from the first DGT transmitting at a first frequency and first phase, and the second signal beam resulting from the first DGT transmitting at the first frequency and second phase; the first and second signal beams resulting from the second DGT being Doppler shifted signals associated with the first DGT first signal beam and the first DGT second signal beam respectively, and determining the fluid velocity flowing through the lumen based on the Doppler shifted signals, the first frequency and the first and second phase signals, and the predetermined angle.

13. The method according to claim 12, wherein the predetermined angle is substantially 12 degrees.

14. The method according to claim 12, wherein the first and second phases are 90 degrees out of phase with one another.

15. An apparatus for determining the velocity of a fluid flowing through a lumen comprising:

a continuous wave (CW) first transducer operable in a first mode for producing a first signal beam, and in a second mode for producing a second signal beam;

a second continuous wave transducer operating as a receiver and coupled to the first transducer at a dihedral angle, the second diffraction grating transducer producing a first beam which intersects the first DGT first beam for receiving a first reflected signal associated with the first signal beam, and for producing a second beam which intersects the first DGT second beam for receiving a second reflected signal associated with the second signal beam;

means for driving the first CW transducer to emit the first and second signal beams at a given frequency and phase;

means for focusing the first beams to intersect in a first predetermined region through which dynamic particles are undergoing velocity analysis, and the second beams to intersect in a second predetermined region through which dynamic particles are undergoing velocity analysis; and means responsive to the first and second reflected signals for comparing parameters associated with the first DGT first and second beams to determine the velocity of the fluid.

16. The apparatus according to claim 15, wherein the first DGT emits the first signal beam at a first frequency, and emits the second signal beam at a second frequency.

17. The apparatus according to claim 15, wherein the first DGT emits the first signal beam at a first frequency and first phase, and emits the second signal beam at the first frequency and a second phase.

18. An apparatus for determining the velocity of blood flowing through a lumen comprising:

a first pair of continuous wave non-diffraction grating transducers coupled at a first dihedral angle relative to one another, the first pair of transducers producing signal beams which intersect at a given point which defines a sensitive volume;

a second pair of continuous wave non-diffraction grating transducers coupled at the first dihedral angle relative to one another; the second pair of transducers producing signal beams which intersect at the given point, the first and second pairs of transducers oriented at a second angle B relative to one another;

means for driving the first and second pairs of transducers to cause one of the first pair to be driven at a first frequency and one of the second pair to be driven at the first frequency; whereby the other of the first pair receives a first reflected signal shifted in frequency relative to the signal from the first pair transmitting transducer, and whereby the other of the second pair receives a second reflected signal shifted in frequency relative to the signal from the second pair transmitting transducer;

electronic circuitry coupled to the first and second pairs of transducers for determining the velocity of the blood taking into account the frequency shifted reflected signals and driving signal frequencies, dihedral angles of the pairs of transducers, and angle between the first and second pairs of transducers.

19. A method of determining the velocity of blood flowing through a lumen comprising:

orthogonally orienting a first pair and a second pair of diffraction grating transducers relative to one another, each transducer of the first and second pairs positioned substantially adjacent one another and having edges converging toward one another so as to form dihedral angles, each the pair of transducers oriented so as to have intersecting beams which produce a sensitive volume around the lumen;

driving a corresponding one of the first and second pairs of transducers to transmit at a first frequency such that a reflected signal indicative of the first frequency is received by the other of the first and second pairs;

adjusting the driving frequency by a predetermined amount and driving the corresponding one of the first and second pairs of transducers to transmit the adjusted frequency such that a reflected signal indicative of the adjusted frequency is received by the other of the first and second pairs;

determining the velocity in the two orthogonal directions based on the frequencies and dihedral angles for each of the first and second pairs of transducers;

calculating the velocity of the blood based on the velocity in the two orthogonal directions.

20. The method according to claim 19, wherein the step of calculating the velocity comprises summing the squares of the of the velocity components and determining the square root of the squares.

* * * * *